(12) United States Patent
Woods et al.

(10) Patent No.: US 6,936,664 B2
(45) Date of Patent: Aug. 30, 2005

(54) REWORKABLE EPOXIDIZED 1-(CYCLO) ALKENYL ETHER/POLYCARBOXYLIC ACID PRODUCT

(75) Inventors: John G. Woods, Farmington, CT (US); Susanne D. Morrill, West Hartford, CT (US); Jianzhao Wang, Ossining, NY (US); Brendan J. Kneafsey, Dublin (IE)

(73) Assignee: Henkel Corporation, Rocky Hill, CT (US)

( * ) Notice: Subject to any disclaimer, the term of this patent is extended or adjusted under 35 U.S.C. 154(b) by 221 days.

(21) Appl. No.: 10/344,944

(22) PCT Filed: Oct. 4, 2001

(86) PCT No.: PCT/US01/31020

§ 371 (c)(1),
(2), (4) Date: May 5, 2003

(87) PCT Pub. No.: WO02/28849

PCT Pub. Date: Apr. 11, 2002

(65) Prior Publication Data

US 2004/0102544 A1 May 27, 2004

(51) Int. Cl.$^7$ .................. C07D 303/12; C08G 59/50; C08L 63/02; H01L 21/56; H01L 23/29

(52) U.S. Cl. .................. 525/523; 257/793; 438/127; 523/427; 523/428; 523/445; 523/457; 523/466; 525/485; 525/486; 525/523; 525/524; 525/533; 528/366; 549/562

(58) Field of Search .................. 257/793; 438/127; 523/427, 428, 445, 457, 466; 525/423, 485, 486, 523, 524, 533; 528/366; 549/562

(56) References Cited

U.S. PATENT DOCUMENTS

| | | | |
|---|---|---|---|
| 3,609,121 A | 9/1971 | Allshwil et al. .......... | 260/47 |
| 3,644,431 A | 2/1972 | Heer et al. .......... | 260/348 A |
| 5,512,613 A | 4/1996 | Afzali-Ardakani et al. | 523/443 |
| 5,536,855 A | 7/1996 | Schultz et al. .......... | 549/539 |
| 5,549,932 A | 8/1996 | Ishidoya et al. .......... | 427/385.5 |
| 5,560,934 A | 10/1996 | Afzali-Ardakni et al. | 424/497 |
| 5,783,867 A | 7/1998 | Belke, Jr. et al. .......... | 257/783 |
| 5,973,033 A | 10/1999 | Ober et al. .......... | 523/443 |
| 6,288,170 B1 | 9/2001 | Waid .......... | 525/113 |

FOREIGN PATENT DOCUMENTS

| | | | |
|---|---|---|---|
| GB | 1 360 811 | 7/1974 | ........... C07D/1/22 |
| JP | 04-325544 | 11/1992 | |
| JP | 05 021516 | 1/1993 | |
| JP | 06 069280 | 3/1994 | |
| JP | 06 077264 | 3/1994 | |
| WO | WO 98/31738 | 7/1998 | ........... C08K/5/09 |

OTHER PUBLICATIONS

M. Sawamato et al., "Selective Vinyl Cationic Polymerization of Monomers with Two Cationically Polymerizable Groups. III. 2–Vinyloxyethyl Glycidal Ether: An Epoxy--Functionalized Vinyl Ether", J. Polym. Sci., Part A 1987, V.25, 2717.

Tofimov et al., "A New Strategy In The Synthesis of Epoxy Resins", Rev. on Heteroatom Chem., V.9, 205, 1993.

*Primary Examiner*—Robert Sellers
(74) *Attorney, Agent, or Firm*—Steven C. Bauman

(57) ABSTRACT

The present invention discloses reworkable epoxy compositions suitable for encapsulation of and underfill for electronic components comprising (a) a curable epoxy component which is the reaction product of an epoxidized 1-alkenyl ether or 1-cycloalkenyl ether and a polycarboxylic acid, the reaction product being substantially free of unreacted acid or acid impurities; and (b) a curing agent for the epoxy component, wherein the reaction products of the epoxy composition are reworkable. The cured epoxy compositions of this invention contain thermally labile weak α-alkoxy ester linkages which provide for the reworkable aspect of the invention.

39 Claims, 1 Drawing Sheet

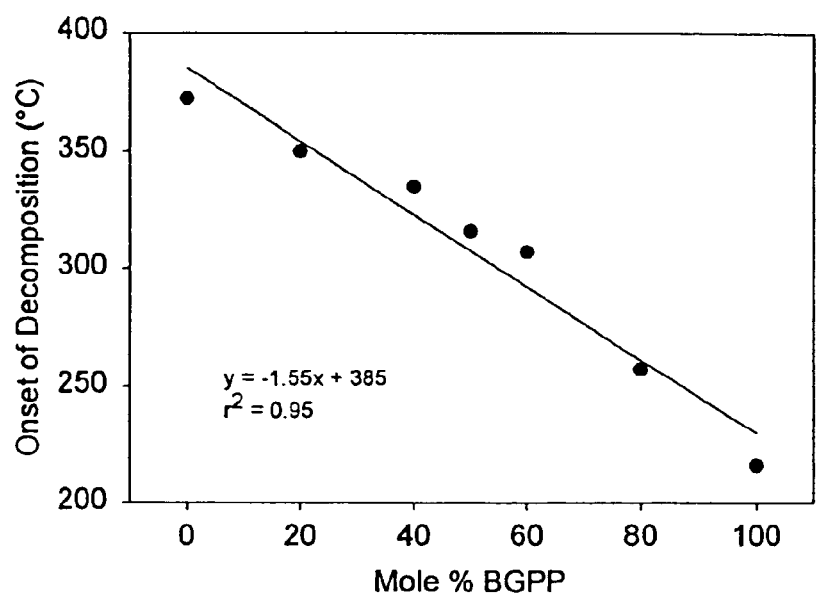
Figure 1. Dependence of degradation onset temperature on concentration of BGPP

REWORKABLE EPOXIDIZED 1-(CYCLO) ALKENYL ETHER/POLYCARBOXYLIC ACID PRODUCT

FIELD OF THE INVENTION:

This invention relates generally to thermosetting resin compositions which are useful for encapsulation of and underfill for electronic components, where easy removal of the components for repair or replacement is required. In particular, this invention relates to reworkable epoxy resins used for mounting onto a circuit board semiconductor devices, such as chip size or chip scale packages (CSPs"), ball grid arrays ("BGAs"), land grid arrays ("LGAs"), and the like, each of which have a semiconductor chip, such as large scale integration ("LSI"), on a carrier substrate.

BRIEF DESCRIPTION OF RELATED TECHNOLOGY

In recent years, the popularity of small-sized electronic appliances, such as camera-integrated video tape recorders ("VTRs") and portable telephone sets, has made size reduction of LSI devices desirable. As a result, CSPs, BGAs, and LGAs are being used to reduce the size of packages substantially to that of bare chips. Such CSPs, BGAs, and LGAs improve the characteristics of the electronic device while retaining many of their operating features, thus serving to protect semiconductor bare chips, such as LSIs, and facilitate testing thereof.

Ordinarily, the CSP/BGA/LGA assembly is connected to electrical conductors on a circuit board by use of a solder connection or the like. However, when the resulting CSP/BGA/LGA circuit board structure is exposed to thermal cycling, the reliability of the solder connection between the circuit board and the CSP/BGA/LGA often becomes suspect. Recently, after a CSP/BGA/LGA assembly is mounted on a circuit board, the space between the assembly and the circuit board is often now filled with a sealing resin (often referred to as underfill sealing) in order to relieve stresses caused by thermal cycling, thereby improving heat shock properties and enhancing the reliability of the structure.

However, since thermosetting resins are typically used as the underfill sealing material, in the event of a failure after the CSP/BGA/LGA assembly is mounted on the circuit board, it is very difficult to replace the assembly without destroying or scrapping the structure in its entirety. Therefore, there has been an ongoing search for resins that will allow easy removal of packaged chip components for recycling, repair or replacement. The cured resins which are being sought are referred to as reworkable in the art.

To that end, techniques for mounting a bare chip on a circuit board are accepted as substantially similar to the mounting of a CSP/BGA/LGA assembly onto a circuit board. Japanese Laid-Open Patent Publication No. 69280/94 discloses a process where a bare chip is fixed and connected to a substrate by use of a resin capable of hardening at a predetermined temperature. In the event of failure, this bare chip is removed from the substrate by softening the resin at a temperature higher than the predetermined temperature. However, no specific resin is disclosed, and there is no disclosure about treating the resin which remains on the substrate.

As pointed out in Japanese Laid-Open Patent Publication No. 77264/94, it is conventional to use a solvent to remove residual resin from a circuit board. However, swelling the resin with a solvent is a time consuming process and the corrosive organic acid ordinarily used as the solvent may reduce the reliability of the circuit board. Instead, that disclosure speaks to a method for removing residual resin by irradiation with electromagnetic radiation.

Japanese Laid-Open Patent Publication No. 251516/93 also discloses a mounting process using a commercially available bisphenol A type epoxy resin (CV5183 or CV5183S; manufactured by Matsushita Electric Industrial Co., Ltd.). However, the removal process so disclosed does not consistently permit easy removal of the chip, the curing step is lengthy at elevated temperatures, and the process generally results in poor productivity.

Thermoplastic underfill resins are known for use in semiconductor chip attachment. See U.S. Pat. No. 5,783,867 (Belke, Jr.). However, such thermoplastic resins tend to leak under relatively modest temperature conditions. In contrast, thermosetting resins cure into a matrix which ordinarily have greater thermal stability under end-use operating temperatures.

U.S. Pat. Nos. 5,512,613 (Afzali-Ardakani) and U.S. Pat. No. 5,560,934 (Afzali-Ardakani), each refer to a reworkable thermoset composition formed from (a) a diepoxide component in which the organic linking moiety connecting the two epoxy groups of the diepoxide includes an acid cleavable acyclic acetal group; (b) an anhydride curing agent; (c) a 1,3-diaza compound and (d) a hydroxy functional initiator. The acid cleavable acyclic acetal groups form the basis of the reworkable composition. The disclosed composition does not, however, allow for reworkability via thermal decomposition.

International Patent Publication No. PCT/US98/00858 refers to a thermosetting resin composition capable of sealing underfilling between a semiconductor device including a semiconductor chip mounted on a carrier substrate and a circuit board to which said semiconductor device is electrically connected. The composition includes about 100 parts by weight of an epoxy resin, about 3 to about 60 parts by weight of a curing agent, and about 1 to about 90 parts by weight of a plasticizer. Here, the area around the cured thermoset is to be heated at a temperature of about 190 to about 260° C. for a period of time ranging from about 10 seconds to about 1 minute in order to achieve softening and a loss of much of its adhesiveness.

U.S. Pat. No. 5,549,932 (Ishidoya) discloses the production of blocked carboxylic acids for use as one-part thermosetting compositions which are formed by the reaction of polycarboxylic acids with vinyl ethers in the presence of acid catalysts, as described in column 5, lines 26–48 and column 7, lines 40–44 of the specification. One reaction product disclosed is a compound having in the molecule two or more carboxyl groups blocked by a vinyl ether group and two or more reactive epoxy groups which may be in the same molecule as the blocked carboxy groups. These products contain an epoxy acetal group as part of a weak α-alkoxy ester linkage used for generating an epoxy curing agent, wherein an α-alkoxy ester is defined here as having an alkoxy group which is alpha to the ethereal oxygen atom of the ester group. For example, these products are initially heated to deblock the polycarboxylic acid via the destruction of the thermally-labile ester linkage. The acid then functions as a curing agent of suitably reactive resins including epoxides, as described in column 7, lines 48–57, in which a polymerization or network forming reaction occurs to give the cured polymeric materials having good chemical and physical properties. Such materials are, however, not suitable for reworkable adhesives due to their lack of a thermally-labile linkage in the cured product, the labile linkage having been destroyed in the heating step used to generate the curing agent. Moreover, the acid catalysts used for the reaction of the polycarboxylic acid with an epoxidized vinyl ether can reduce the storage stability of the epoxide monomer and reduce the degradation temperature of the cured adhesive to a temperature below that which is useful for maintenance of its intended application, such as for an underfill for electronic components where stability during thermal cycling is required.

U.S. Pat. No. 5,973,033 (Ober) discloses compounds providing reworkable cured thermosets which contain two cyclic hydrocarbon moieties which are substituted, for example, with an epoxy group to provide crosslinking functionality, and which are linked to each other by a secondary or tertiary oxycarbonyl-containing moiety for formation of an epoxidized secondary or tertiary ester which, when cured provides a composition which decomposes at moderate temperatures. An acetal group is not present in these compounds. A disadvantage of these compounds is that they are difficult and costly to synthesize, requiring several synthesis steps, expensive reagents and extensive use of solvents.

Thus, current reworkable epoxies require the use of strong acid and/or high temperatures in order to achieve their reworkablity. Other current reworkable resins are either expensive and difficult to make, or use solvents which are undesirable. It would be desirable for an underfilling sealing material to provide good productivity and thermal shock properties, while allowing the substrates, e.g. circuit boards, with which it is to be used to be readily processed and easily separated from a semiconductor device, without application of strongly acidic media or elevated temperature conditions that may compromise the integrity of the semiconductor devices remaining on the substrate or the substrate itself. It would further be desirable to provide an easy and cost-effective method for synthesizing an epoxy resin comound, which when cured provides a reworkable thermosetting composition, the method for which would ideally employ raw materials which are commercially available and which could be performed without acid catalysts and without solvents. It would also be beneficial to provide a means for lowering the decomposition temperature of cured formulations of commercially available epoxide monomers by providing an additive for thermosettting resin compositions which is substantially free of unreacted acid or acidic impurities and which is the reaction product of an epoxidized 1-alkenyl ether or 1-cycloalkenyl ether and a polycarboxylic acid.

SUMMARY OF THE INVENTION

The present invention provides a thermosetting epoxy resin composition, which when cured provides a composition which is reworkable and is suitable for encapsulation of or underfill for electronic components. The invention includes a curable epoxy resin component which is the reaction product of an epoxidized 1-alkenyl ether or 1-cycloalkenyl ether and a polycarboxylic acid wherein the reaction product is substantially free of unreacted acid or acid impurities; and a curing agent for the epoxy component, such as an amine compound or a heterocyclic amine compound, such as an imidazole compound, or a combination thereof.

Reaction products of these compositions are capable of softening under exposure to elevated temperature conditions, such in excess of the temperatures used to cure the composition. Such temperature exposure combined with the epoxy compound having at least one thermally cleavable linkage provides the reworkable aspect of this invention. An additional reworkable aspect is achieved by exposing the reaction products of these compositions to dilute acid.

In another aspect of the invention there is provided curable epoxy resin compounds which may be represented by the following formulas:

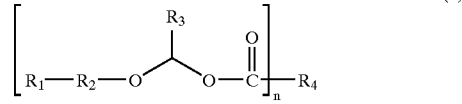

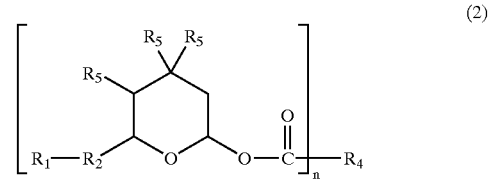

wherein $R_1$ may be aliphatic or cycloaliphatic epoxy moiety; $R_2$ may be a $C_{1-15}$ alkyl, alkenyl, aryl, alkaryl, cycloalkyl, cycloalkenyl, alkyl ether or alkyl ester group; $R_3$ may be a $C_1$-8 alkyl, alkenyl, aryl, alkaryl, cycloalkyl, or cycloalkenyl group; $R_4$ may be an n-valent $C_{1-30}$ alkyl, alkenyl, aryl, alkaryl, cycloalkyl, cycloalkenyl, alkyl ether or alkyl thioether group that may be unsubstituted or substituted such as with halogen, hydroxyl or alkoxy groups; $R_5$ may be independently hydrogen, methyl or ethyl groups; and n is an integer from 2 to 4.

The epoxide-based curable compounds include cycloaliphatic epoxy, as well as aliphatic epoxy compounds. An example of a useful cycloaliphatic epoxide moiety is one having the following formula:

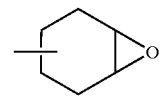

The present invention further provides a reworkable epoxy composition, which when cured provides a composition which is decomposable and is suitable for encapsulation of or underfill for electronic components, the reworkable composition including: (a) a curable epoxy component which is formed from the reaction of an epoxidized 1-alkenyl ether or 1-cycloalkenyl ether and a polycarboxylic acid and is substantially free of unreacted acid or acidic impurities, said curable epoxy component being present in an amount within the range of about 20 to about 65 weight percent, based on the total weight of the composition; (b) a primary or secondary amine curing agent in an amount within the range of about 0.5 to about 2.0 equivalents of amine per equivalent of epoxide; (c) an inorganic filler component in an amount up to about 60 weight percent, based on the total weight of the composition; and a flowability agent in an amount up to about 0.5 weight percent, based on the total weight of the composition.

The inventive reworkable epoxy composition is particularly useful as an underfilling sealing resin, and enables a semi-conductor device, such as a CSP/BGA/LGA assembly which includes a semi-conductor chip mounted on a carrier substrate, to be securely connected to a circuit board by short-time heat curing and with good productivity. Reaction products of the inventive compositions demonstrate excellent heat shock properties, also referred to as thermal cycle properties, and permit the semi-conductor device to be easily removed from the circuit board by localized heating or dilute acid in the event of semiconductor device or connection failure. This makes it possible to reuse the circuit board (with the remaining functioning semi-conductor devices still electrically attached) and thereby achieve an improvement in the yield of the production process and a reduction in production cost.

The compositions of this invention may also be used for micro-electronic applications beyond sealing underfill, such as with glob top, die attachment and other applications for thermosetting compositions in which rapid cure time and an extended useful working life are desirable.

The epoxy resin component of the composition of the present invention is also useful as an additive for lowering the decomposition temperature of a cured formulation of a commercially available epoxy monomer. Such an epoxy additive provided by the present invention is a curable epoxy compound which is the reaction product of an epoxidized 1-alkenyl ether or 1-cycloalkenyl ether and a polycarboxylic acid, wherein the reaction product is substantially free of unreacted acid or acid impurities.

In yet another aspect of the invention there is provided a method for synthesizing an epoxy monomer which includes reacting an epoxidized 1-alkenyl ether or 1-cycloalkenyl compound with a polycarboxylic acid. Desirable the reaction ratio includes at least one equivalent of the ether per equivalent of the carboxylic acid in the absence of acid catalysts. The reaction products are desirably substantially free of unreacted acid or acid impurities. The reaction of the vinyl ether with the polycarboxylic acid can be performed in the absence of solvents. This method employs raw materials which are commercially available.

The invention further provides for a method for preparing a thermosetting epoxy resin composition, which when cured provides a composition which is reworkable and which is suitable for encapsulation of or underfill for electronic components. The inventive method includes combining in admixture: (a) a curable epoxy component which is the reaction product of an epoxidized 1-alkenyl ether or 1-cycloalkenyl ether and a polycarboxylic acid; and (b) an amino-containing or thio-containing curing agent component and permitting the admixture to cure. Amino-containing curing agents include amines, heterocyclic amines or combinations thereof.

Furthermore, a means for lowering the decomposition temperature of cured formulations of commercially available epoxide monomers is disclosed, wherein the method includes admixing: (a) a curable epoxy component which is the reaction product of an epoxidized 1-alkenyl ether or 1-cycloalkenyl ether and a polycarboxylic acid, wherein the reaction product is substantially free of unreacted acid or acid impurities; (b) an amino-containing or thiol-containing curing agent component; and (c) a commercially available epoxy monomer, such as an epoxidized diglycidyl ether of a bisphenol. The curable epoxy component of the reworkable epoxy compositions provided by the present invention serve as the additive which lowers the decomposition temperature of the cured formulation of the commercially epoxy resin monomer, thereby increasing the workability of commercially available monomers upon cure.

Other benefits and advantages of the present invention are discussed below.

BRIEF DESCRIPTION OF THE DRAWINGS

FIG. 1 is a graph depicting the dependence of the onset temperature of decomposition ($T_d$) of cured epoxy compositions of the present invention on the concentration of bis-(alpha-glycidoxypropyl) pimelate (BGPP), an inventive epoxy monomer compound.

DETAILED DESCRIPTION OF THE INVENTON

The reworkable epoxy resin compositions provided by the present invention which are useful for encapsulation of and underfill for electronic components, include: a) a curable epoxy component, which is the reaction product of an epoxidized 1-alkenyl ether or 1-cycloalkenyl and a polycarboxylic acid; and (b) a curing agent component for the epoxy component, such as an amine or heterocyclic amine compound or a thiol. Reaction products of these compositions are capable of softening under exposure to elevated temperature conditions, such as an excess of the temperature chosen to cure the composition. Loss of adhesion to the substrate occurs at temperatures greater than that which was used to cure the composition. For instance, at least about 50 percent of adhesion to the substrate is typically lost at temperatures in excess of about 200° C. Furthermore, the reaction products of the compositions of the present invention decompose in dilute acid which provides an additional reworkable aspect.

The reworkable epoxy compositions provided by the present invention may optionally further contain one or more inorganic filler components. The inorganic filler component may include reinforcing silicas, such fused silicas, and may be untreated or treated so as to alter the chemical nature of their surface. Particularly desirable ones have a low ion concentration and are relatively small in particle size (e.g., in the range of about 2–10 microns, such as on the order of about 2 microns), such as the silica commercially available from Admatechs, Japan under the trade designation SO-E5. Other desirable materials for use as the inorganic filler component include those constructed of or containing aluminum oxide, silicon nitride, aluminum nitride, silica-coated aluminum nitride, boron nitride and combinations thereof.

The curing agent components include materials capable of catalyzing the polymerization of the epoxy resin component of the inventive compositions. Desirable curing agents for use with the present invention include amino-containing compounds, such as amines and heterocyclic amines, such as imidazoles.

Desirable amines useful as curing agents for the present compositions include dicyandiamide, diethylenetriamine, triethylenetetramine, diethylaminopropylamine, m-xylenediamine, diaminodiphenylamine, isophoronediamine, menthenediamine, polyamides, and combinations thereof.

Useful heterocyclic amines for use as curing agents include, without limitation, the following imidazole compounds: imidazole, isoimidazole, 2-methyl imidazole, 2-ethyl-4-methylimidazole, 2,4-dimethylimidazole, butylimidazole, 2-heptadecenyl-4-methylimidazole, 2-undecenylimidazole, 1-vinyl-2-methylimidazole, 2-n-heptadecylimidazole, 2-undecylimidazole, 2-heptadecylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole, addition products of an imidazole and trimellitic acid, addition products of an imidazole and 2-n-heptadecyl-4-methylimidazole, phenylimidazole, benzylimidazole, 2-methyl-4,5-dephenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4-,5-diphenylimidazole, 2-(2-hydroxyphenyl)-4,5-diphenylimidazole, di(4,5-diphenyl-2-imidazole)-benzene-1,4,2-naphthyl-4,5-diphenylimidazole, 1-benzyl-2methylimidazole, 2-p-methoxystyrylimidazole, and combinations thereof.

Imidazole compounds and tertiary amines are examples of useful catalytic epoxy resin curing agents which are typically used in an amount of from about 0.01 to about 10% by weight of the epoxy resin component.

Primary and secondary amine curing agents are typically used in an amount of from about 0.5 to about 2.0 equivalents of amine per equivalent of epoxide. Desirably, primary and secondary amine curing agents are used in an amount of about 1 equivalent of amine per equivalent of epoxide.

The curing agent is bis-(para-aminocyclohexyl)methane is a particularly desirable curing agent useful in the present invention.

Further components may be added to provide the physical properties and characteristics for the compositions and reaction products to render the compositions attractive for commercial use, particularly the micro-electronics industry. For example, the composition may further include a flowability agent, such as a silane and/or titanate. Appropriate silanes for use herein include octyl trimethoxy silane, (commercially available from OSI Specialties Company, Danbury, Conn. under the trade designation A-137), and methacryloxy propyl trimethoxy silane (commercially available from OSI under the trade designation A-174).

Appropriate titanates for use as flowabililty agents include titanium for tetrakis [2,2-bis [(2-propepnyloxy)methyl]-1-butanolato-0], [bis(ditridecylphosphito-0)-dihydrogen]$_2$ (commercially available from Kenrich Petrochemical, Inc., Bayonne, N.J. under the trade designation KR-55). Combinations of these compounds may also be useful. Desirably the flowability agent is used in an amount up to about 2 parts by weight per 100 parts by weight of the epoxy resin compounds. In one embodiment, the composition of the present invention has a viscosity in the range of about 500–70,000 cps.

The composition of the present invention may further include adhesion promoters, such as the silanes, glycidyl trimethoxysilane (commercially available from OSI under the trade designation A-187) or gamma-amino propyl tri-ethoxysilane (commercially available from OSI under the trade designation A-1100).

Cyanate esters may also be used in the inventive compositions. Useful cyanate esters include dicyanatobenzenes, tricyanatobenzenes, dicyanatonaphthalenes, tricyanatonaphthalenes, dicyanatobiphenyl, bis(cyanatophenyl)methanes and alkyl derivatives thereof, bis(dihalocyanatophenyl)propanes, bis(cyanatophenyl)ethers, bis(cyanatophenyl)sulfides, bis(cyanatophenyl)propanes, tris(cyanatophenyl)phosphites, tris(cyanatophenyl)phosphates, bis(halocyanatophenyl)methanes, cyanated novolac, bis[cyanatophenyl(methylethylidene)]benzene, cyanated bisphenol-terminated thermoplastic oligomers, and combinations thereof.

In one particular useful embodiment, the reworkable epoxy resin compositions of the present invention include (a) a curable epoxy component which is the reaction product of an epoxidized 1-alkenyl ether or 1-cycloalkenyl ether and a polycarboxylic acid, the reaction product being substantially free of unreacted acid or acid impurities, said component being present in an amount within the range of about 20 to about 65 weight percent, based on the total weight of the composition; (b) a primary or secondary amine curing agent for the epoxy component in an amount within the range of about 0.5 to about 2.0 equivalents of amine per equivalent of epoxide; (c) optionally, an inorganic filler component in an amount of about 0 weight percent to about 60 weight percent, based on the total weight of the composition; and (d) optionally a flowability agent in an amount of about 0 weight percent to about 0.5 weight percent, based on the total weight of the composition.

The curable epoxy compounds of the present invention may be represented by the following formulas:

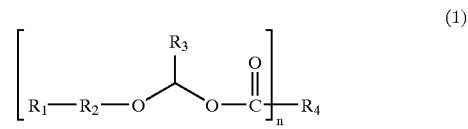

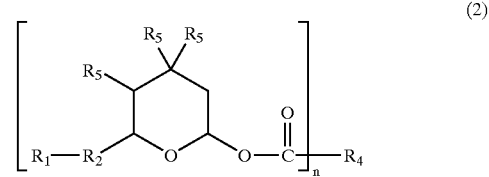

wherein $R_1$ may be an aliphatic or cycloaliphatic epoxy moiety; $R_2$ may be a $C_{1-15}$ alkyl, alkenyl, aryl, alkaryl, cycloalkyl, cycloalkenyl, alkyl ether or alkyl ester group; $R_3$ may be a $C_{1-8}$ alkyl, alkenyl, aryl, alkaryl, cycloalkyl, or cycloalkenyl group; $R_4$ may be an n-valent $C_{1-30}$ alkyl, alkenyl, aryl, alkaryl, cycloalkyl, cycloalkenyl, alkyl ether or alkyl thioether group that may be unsubstituted or substituted such as with halogen, hydroxyl or alkoxy groups; $R_5$ may be independently hydrogen, methyl or ethyl groups; and n is an integer from 2 to 4.

In one desired embodiment of the invention, the curable epoxy component is the diepoxide, bis-(α-glycidoxypropyl) glutarate. Another suitable curable epoxy component for the reworkable epoxy compositions of the invention is the diepoxide, bis-(α-glycidoxypropyl) pimelate. A further suitable curable epoxy component of the reworkable epoxy compositions of this invention is the diepoxide, bis-[α-(2-glycidoxyethoxy)ethyl] glutarate.

As described above, the reaction products of the compositions of the present invention are capable of softening under exposure to elevated temperature conditions, which are generally in excess of a temperature chosen to cure the composition. This allows a loss of adhesion to the substrate to occur at temperatures greater than that which was used to cure the composition. In particular, when the curable epoxy component is the diepoxide, bis-(α-glycidoxypropyl) pimelate, and the amino-containing curing agent for the epoxy component is bis-(para-aminocyclohexyl)methane, the composition has an onset temperature of decomposition ($T_d$) of about 216° C. Furthermore, a reworkable epoxy composition of the invention containing a curable epoxy component which is the diepoxide, bis-[α-(2-gylcidoxyethoxy)ethyl]glutarate, and cured by the amino-containing curing agent bis-(para-aminocyclohexyl) methane, the reworkable composition has an onset temperature of decomposition of about 230° C.

In general, the reworkable epoxy compositions of this invention have decomposition temperatures significantly lower than those of cured formulations of commercially available epoxy monomers, such as diglycidyl ethers of bisphenol A or F, glycidyl ethers of phenol formaldehyde resins, and glycidyl ethers of polyols. For example, the decomposition temperature of a cured formulation of a commercial epoxidized diglycidyl ether of bisphenol F, cured with bis-(para-aminocyclohexyl)methane, is approximately 370° C. For that reason, the curable epoxy component of the reworkable epoxy compositions of this invention have been found to be useful as additives for lowering the decomposition temperature of cured formulations of commercially available epoxy monomers. In particular, the additive of the present invention is a curable epoxy component which is the reaction product of an epoxidized 1-alkenyl ether or 1-cycloalkenyl ether and a polycarboxylic acid, wherein the additive is substantially free of unreacted acid or acid impurities. The additive may be presented by the formulas previously set forth.

In one desirable embodiment of the present invention, there is provided a curable epoxy composition which includes as an additive to a conventional commercially available epoxy monomer composition, one or more of the diepoxide compounds selected from bis-($\alpha$-glycidoxypropyl)glutarate, bis-($\alpha$-glycidoxypropyl) pimelate, and bis-[$\alpha$-(2-glycidoxyethoxy)ethyl]glutarate. There aditives lower the thermal decomposition temperature of conventional, commercially available epoxy monomer compositions, such as those which include a diglycidyl ether of bisphenol F, a glycidyl ether of a polyol or a glycidyl ether of a formaldehyde resin.

The present invention further provides for a method of lowering the decomposition temperature of a cured formulation of a commercially available epoxy resin monomer, wherein the method includes admixing: (a) a curable epoxy component of the present invention which is the reaction product of an epoxidized 1-alkenyl ether or 1-cycloalkenyl ether and a polycarboxylic acid, wherein the reaction product is substantially free of unreacted acid or acid impurities; (b) a commercially available epoxy monomer which desirably includes an epoxidized diglycidyl ether of a bisphenol such as bisphenol F; and (c) an amino-containing or thiol-containing curing agent for the epoxy components, wherein the curing agent is desirably an amine or heterocyclic amine compound, and wherein the resultant epoxy composition is thermally decomposable. This method may further include the step of admixing an inorganic filler component into the composition.

The present invention further provides for a method for preparing a reworkable epoxy composition, which when cured provides a composition which is thermally decomposable, said method including admixing: (a) a curable epoxy component which is the reaction product of an epoxidized 1-alkenyl ether or 1-cycloalkenyl ether and a polycarboxylic acid and (b) a curing agent for the epoxy component. Desirably the reaction product is substantially free of unreacted acid or acid impurities. The curing agents include amino-containing and thiol-containing agents. Amines and heterocyclic amines are examples of amino-containing curing agents. This method may further include admixing an inorganic filler component into the composition.

The present invention also provides for a method for synthesizing an epoxy monomer substantially free of unreacted acid and/or acid impurities is herein disclosed. This method includes reacting an epoxidized 1-alkenyl ether or 1-cycloalkenyl ether compound with a polycarboxylic acid at a ratio of at least one equivalent of the ether per equivalent of the polycarboxylic acid in the absence of acidic catalysts. Reaction conditions may vary depending on the epoxy monomer which is to be formed. However typically the reaction is performed at a temperature of about 80 to about 100° C. for about 2 to about 50 hours in the absence of an acid catalyst and in the absence of solvent. In one embodiment of the invention, the epoxy monomer is the diepoxide, bis-($\alpha$-diglycidoxypropyl) glutarate. This monomer is formed from the reaction of 1-propenylglycidyl ether and glutaric acid. The commercially available 2-propenylether epoxide compound is isomerized to 1-propenyl ether epoxide in the presence of a ruthenium catalyst or other epoxide compatible catalyst. Glutaric acid is also commercially available. Thus, the reactants necessary for formation of the epoxy monomer in the present invention are either commercially available or can be readily synthesized from commercially available raw materials.

In another embodiment of the inventive method, the epoxy monomer is the diepoxide, bis-($\alpha$-glycidoxypropyl) pimelate which can be formed from the reaction of 1-propenylglycidyl ether and the polycarboxylic acid, pimelic acid.

The epoxy monomer formed from the present method can also be the diepoxide, bis-[$\alpha$-(2-glycidoxyethoxy)ethyl] glutarate, which is formed from the reaction of 2-vinyloxyethylglycidyl ether and the polycarboxylic acid, glutaric acid. The synthesis of 2-vinyloxyethylglycidyl ether has been previously described by M. Sawamato et al., *J. Polym. Sci., Part A*, 1987, 25, 2717, the subject matter of which is incorporated herein by reference.

In general, any 2-alkenylether epoxide that can be isomerized into the corresponding 1-propenyl derivative may be used as the starting compound for the formation of the 1-alkenyl ether compound reactant. Alternatively, already formed 1-alkenyl ethers such as vinylglycidyl ether may be employed directly without the need to conduct the isomerization reaction. Such materials are not commercially available at present, but may be in the future.

The present invention further includes a method of assembling an electronic component which includes the step of applying the reworkable epoxy composition of the present invention to a surface of an electronic component. To that end, an electronic device is also provided by this invention wherein the device includes a semi-conductor device and a circuit board to which the semi-conductor device is electrically connected, the device itself being assembled using a reworkable epoxy composition according to the present invention.

The reworkable epoxy compositions of the present invention may be of the 1-pack type, in which all the ingredients are mixed together, or of the 2-pack type in which the curable component(s), is (are) included in one part and the curing agent is stored separately in a second part, and mixed together only prior to use.

During application, the reworkable epoxy compositions according to the present invention penetrate and flow readily into the space between the semi-conductor chip and the circuit board, or at least show a reduction in viscosity under heated or use conditions thus penetrating and flowing easily.

Generally, it is desirable to prepare the reworkable epoxy resin compositions of this invention by selecting the types and proportions of various components to reach a viscosity at a temperature of 25° C. in the range of 500 to 70,000 cps, depending on the amount present (if any) of an inorganic filler component, so as to improve its ability to penetrate into the space (e.g., of 10 to 200 $\mu$m) between the circuit board and a semi-conductor device. At this viscosity, the gel times of the compositions will also be tailored to a specified period of time (such as 15 seconds, or 1 or 2 minutes) at a temperature of about 150° C. With such a gel time, the compositions penetrate into the space between the circuit board and the semiconductor device relatively rapidly, and allow for a greater number of assemblies to be filled without observing a viscosity increase in the composition thereby rendering it less effective for application.

Using a suitable application means, such as a dispenser, a thermosetting resin composition in accordance with this invention can be applied to the periphery of an electronically-connected semi-conductor chip. The composition penetrates by capillary action into the space between the carrier substrate, i.e. circuit board, and the semiconductor chip. The thermosetting resin composition is then thermally cured by the application of heat.

Reworkable epoxy compositions of the present invention may ordinarily be cured by heating to a temperature in the range of about 120 to about 180° C. for a period of time of about 0.5 to 30 minutes. However, generally after application of the composition, initial cure time of about 1 minute sets up the composition, and complete cure is observed after about 5 to about 15 minutes at 165° C. Thus the composition of the present invention can be used at relatively moderate temperatures and short-time curing condition, and hence achieve very good productivity.

The amount of the reworkable epoxy composition applied should be suitably adjusted so as to fill almost completely the space between the carrier substrate and a semi-conductor chip, which amount, of course, may vary depending on application.

Cured reaction products of the reworkable epoxy compositions of the present invention demonstrate excellent adhesive force, heat resistance and electric properties, and acceptable mechanical properties, such as flex-cracking resistance, chemical resistance, moisture resistance and the like, for the applications for which they are used herein.

In the mounting process, by using the reworkable epoxy composition of the present invention, after the semi-conductor device is mounted on the circuit board, the resulting structure is tested with respect to characteristics of the semi-conductor device, connection between the semi-conductor device and the circuit board, other electrical characteristics, and the state of sealing. In the event a failure is found, repair can be made in the manner detailed below.

The area around the semi-conductor device which has failed is heated at a temperature of about 190 to about 260° C. for a period of time ranging from about 10 seconds to about 1 minute. Desirably, the temperature should be maintained in the range of about 210 to about 230° C. and the period of time should be within the 30 seconds to 1 minute range. Although no particular limitation is placed on the way in which heating occurs, localized heating is particularly desirable, such as the application of hot air to the failure site by a heating gun.

As soon as the resin is softened by partial decomposition to cause a reduction in bond strength, the semi-conductor device may be pulled apart and removed from the carrier substrate, such as with tweezers or pliers. Any residue remaining from the cured product of the reworkable epoxy compositions can be removed, for example by scraping it off after the residue has been softened by heating it to a predetermined temperature.

Alternatively, the epoxide formulations can be dissolved by hydrolysis of one or more cleavable links. The cleavable links are generally cleaved in aqueous acid, but in order to dissolve the network fragments, an organic solvent may also be necessary. Solvent mixtures containing an alcohol and organic acid are suitable for reworking the cured resin.

Useful organic acids include, but are not limited to, methanesulfonic acid and p-tolulenesulfonic acid.

The present invention will be more readily appreciated with reference to the examples which follow.

EXAMPLES

Example 1

Synthesis of 1-Propenyl Glycidyl Ether (PGE)

This example describes a method for preparing 1-propenyl glycidyl ether (PGE), a 1-alkenyl ether, from readily available and inexpensive reagents. The reaction scheme is illustrated below. Once formed, this compound becomes a useful reactant to make reworkable epoxy compounds and compositions in accordance with the present invention.

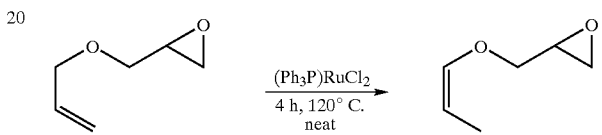

To a 1-liter reaction flask equipped with a magnetic stirrer, condenser, thermocouple, nitrogen inlet and heating mantel was added allyl glycidyl ether (342 g; 3.0 moles) and tris(triphenylphosphonium)ruthenium (II) chloride (5.23 g; 5.45 millimoles). The mixture developed a brown color as the catalyst was dissolved. The solution was stirred and heated to 120° C. under a nitrogen atmosphere. After 4 hours, the reaction mixture was cooled to room temperature and distilled under vacuum to give the isomerized product, 1-propenyl glycidyl ether as a colorless liquid, b.p. 58–62° C. at 20 torr (304 g, 89% yield). The structure of the product was confirmed from $^1$H NMR and IR spectra and found to be a 3:2 blend of Z:E isomeric forms.

PGE monomer has two different reactive functional groups, viz. an epoxide and a 1-propenyl ether. We have discovered that PGE may be reacted with carboxylic acids exclusively through the propenyl ether group when there is at least one equivalent of propenyl ether per equivalent of carboxylic acid present in the reaction mixture. The reaction may be conducted neat (without added solvent) and in the absence of an acidic catalyst, which is typically employed in the syntheses of conventional α-alkoxy esters.

Example 2

Synthesis of Bis-(α-glycidoxypropyl)Glutarate (BGPG)

This example describes a method for preparing, in the absence of undesirable acidic catalysts, curable epoxidized compounds according to the invention which are reaction products of PGE prepared in Example 1 and a commercially available polycarboxylic acid, glutaric acid. The reaction scheme is illustrated below.

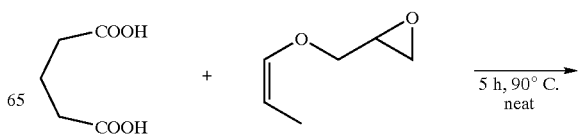

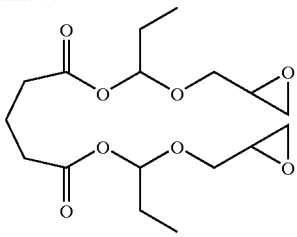

To a 250 ml reaction flask equipped with a magnetic stirrer heating mantel and thermocouple was added PGE (50.0 g, 0.439 moles) and glutaric acid (24.6 g, 0.187 moles). The mixture was heated to 90° C., during which time the acid dissolved in the PGE. Heating and stirring were continued for 5 hours. The reaction mixture was cooled to room temperature, dissolved in acetone (200 mL) and filtered through a short column of basic alumina to remove traces of unreacted acid. The solvent and excess PGE were removed by distillation under reduced pressure to give the bis-(α-glycidoxypropyl)glutarate (BGPG) (38.1 g; 57% yield) as a colorless liquid. The structure of the product was confirmed by $^1$H NMR and IR. analyses.

Example 3
Synthesis of Bis-(α-glycidoxypropyl)Pimelate (BGPP)

This example describes the process of preparing the reworkable epoxide compound BGPP in accordance with the present invention. The reaction scheme is illustrated below.

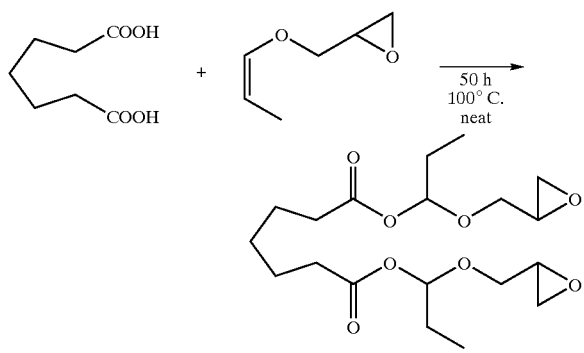

To a 250 ml reaction flask equipped with a magnetic stirrer, heating mantel and thermocouple was added PGE (66.3 g, 0.58 moles) and pimelic acid (40.0 g, 0.25 moles). The mixture was heated and stirred at 100° C. for 50 hours. After cooling to 65° C., the reaction flask was connected to a vacuum pump and excess PGE was removed over 3 hours at a pressure of 350 mtorr. Bis-(α-glycidoxypropyl)pimelate (BGPP) was isolated in quantitative yield as a viscous oil. The structure of the product was confirmed by $^1$H NMR and IR analyses.

Example 4
Thermal Analysis of BGPP Epoxide Compositions with Controlled Decomposition The curing and thermal decomposition of epoxide compositions containing bis-(α-glycidoxypropyl)pimelate (BGPP) were investigated by differential scanning calorimetery (DSC) and thermogravimetric analysis (TGA) respectively. The monomer has an epoxide equivalent weight (EEW) of 194 g/mole. For comparative purposes, a composition containing a conventional commercially available epoxy monomer, bisphenol F diglycidyl ether (BPF), having EEW of 165 g/mole, was also examined. The compound, bis-(para-aminocyclohexyl)methane (PACM), having an amine equivalent weight of 52.5 g/mole, was employed as curing agent. A series of compositions containing varying amounts of both epoxide monomers were also prepared to determine the effect of increasing concentration of BGPP on the decomposition temperature. The compositions A–G were prepared by blending together the epoxy monomer(s) and curing agent in stoichiometric proportions (i.e. the combined equivalence of the epoxide monomers equals that of the amine) as listed in Table 1. In all cases, homogeneous blends were obtained after mixing for about 5 minutes and the compositions were analyzed as soon as the blending was complete or stored in a freezer at −26° C. until needed.

TABLE 1

Epoxy-amine Compositions Containing Bis-(α-glycidoxypropyl) Pimelate (BGPP), Prepared as Described in Example 3. All Amounts are in Equivalents.

| Composition | BGPP | BPF | PACM |
| --- | --- | --- | --- |
| A | 0 | 1.0 | 1.0 |
| B | 0.2 | 0.8 | 1.0 |
| C | 0.4 | 0.6 | 1.0 |
| D | 0.5 | 0.5 | 1.0 |
| E | 0.6 | 0.4 | 1.0 |
| F | 0.8 | 0.2 | 1.0 |
| G | 1.0 | 0 | 1.0 |

BGPP: bis-(α-glycidoxypropyl) pimelate
BPF: bisphenol F diglycidyl ether
PACM: bis-(para-aminocyclohexyl)methane DSC analysis was conducted on the uncured compositions at a heating rate of 5° C./minute. The temperatures of the onset of curing and maximum curing rate (peak max.) and the enthalpy of the curing reaction were recorded and the data are presented in Table 2. All compositions show onsets of curing in the range 54–69° C. These values are not significantly different from one another and the results are understandable since the epoxide groups of BGPP and BPF are similar in structure (i.e. both are unsubstituted glycidoxy groups) and are expected to be similar in reactivity with amines. The peak maximum values are not significantly different from one another at concentrations of BGPP ranging from 0–80 mole % (compositions A–F). At concentrations in excess of this value, the peak maximum is shifted to a slightly higher temperature (114° C.; formulation G). This shift is attributed to the slightly slower curing rate of the composition G resulting from the slightly higher equivalent weight of monomer BGPP compared to BPF. This difference in curing rate is also reflected in the enthalpy, which decreases steadily with increasing concentration of BGPP.

TABLE 2

DSC Analysis of Epoxy/Amine Compositions

| Composition | Mole % BGPP | Onset of Cure ° C. | Peak Max. ° C. | Enthalpy J/g |
| --- | --- | --- | --- | --- |
| A | 0 | 69 | 99 | 437 |
| B | 20 | 59 | 93 | 439 |
| C | 40 | 59 | 95 | 422 |
| D | 50 | 54 | 95 | 374 |
| E | 60 | 56 | 97 | 396 |
| F | 80 | 56 | 101 | 368 |
| G | 100 | 62 | 114 | 293 |

The thermal decomposition of cured compositions A–G was determined by TGA. About 15 mg quantities of each composition A–G were placed in separate TGA pans and cured isothermally on the balance of a thermogravimetric analyzer by heating at 90° C. for 3 hours. No significant weight losses were recorded during these curing experiments. As soon as the curing time was complete, the temperature was increased from 90° C. to 600° C. at a heating rate of 20° C. minute and the change in sample weight was recorded as a function of temperature. The onset of decomposition ($T_d$) was determined by step-analysis of the weight-loss plot. The temperature corresponding to a weight loss of 10% was also recorded. The results are presented in Table 3.

TABLE 3

TGA Analysis of Cured Compositions A–G

| Composition | Mole % BGPP | $T_d$ (° C.) | Temperature at 10% weight loss (° C.) |
|---|---|---|---|
| A | 0 | 372 | 381 |
| B | 20 | 350 | 350 |
| C | 40 | 335 | 308 |
| D | 50 | 316 | 286 |
| E | 60 | 307 | 278 |
| F | 80 | 257 | 258 |
| G | 100 | 216 | 229 |

As the concentration of BGPP is increased, there is a decrease in the onset temperature of decomposition ($T_d$) and the temperature corresponding to a 10% weight loss. In addition, the decrease in $T_d$ was found to correlate linearly with inverse concentration of BGPP to a high degree of accuracy (see FIG. 1). The epoxy monomer, BGPP, may therefore be used as an additive of the conventional monomer BPF to control its decomposition temperature.

Example 5

Synthesis of bis-[α-(2-glycidoxyethoxy)ethyl]glutarate (BGEG)

This example shows the preparation of another epoxidized compound according to this invention, bis-[α-(2-glycidoxyethoxy)ethyl]glutarate (BGEG) which is formed, in the absence of undesirable acidic catalysts, from the reaction of a 1-alkenyl ether (synthesized by the method of Sawamoto, et al. using readily available reagents) and a commercially available polycarboxylic acid (i.e. glutaric acid). The reaction scheme is illustrated below.

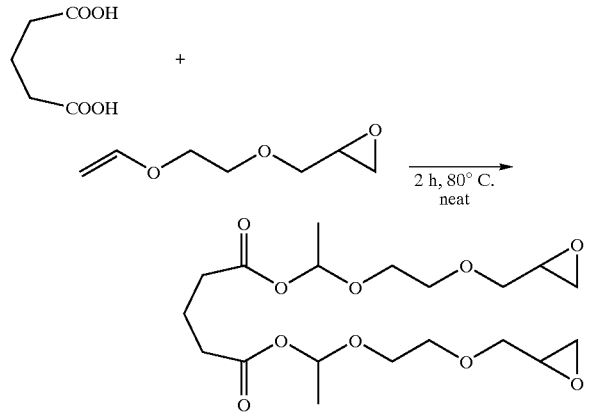

Glutaric acid (1.32 g; 0.01 moles) was added slowly over about 20 minutes to a stirred reaction flask containing 2-vinyloxyethyl glycidyl ether (prepared as described by Sawamoto et. Al in *J. Polym. Sci.*, Part A 1987, V. 25, 2717) at 80° C. After all the acid was added, heating and stirring was continued for a further 2 hours. On cooling, the product, bis-[α-(2-glycidoxyethoxy)ethyl]glutarate, was obtained in quantitative yield. The structure of the product was confirmed by $^1$H NMR and IR analysis. Previous synthesis of polyepoxides by addition of 2-vinyloxyethyl glycidyl ether to polycarboxylic acids has previously been reported to occur in the presence of acid catalysts by Tofimov et. al (*Review Heteroatom Chem.* 1993, V.9, 205). Such catalysts are undesirable as they tend to reduce the storage stability of the epoxide monomer and reduce the degradation temperature of the cured adhesive polymer.

Example 6

Thermolysis of bis-[α-(2-glycidoxyethoxy)ethyl]glutarate (BGEG)

Thermogravimetric (TG) analysis of BGEG showed the onset of weight loss occurs at 176° C. (heating rate 10° C./minute). Since this is a far lower value than is predicted for the volatilization of an organic compound of molecular weight of 420, the weight loss may be attributed to a thermally induced decomposition of the monomer. Gas chromatographic (GC) analysis of BGEG (100–250° C. at 16° C./minute; injector temperature 250° C.; capillary column) shows that the monomer decomposes quantitatively to form the two starting reagents 2-vinyloxyethyl glycidyl ether (3.2 minutes) and glutaric acid (5.4 minutes). This experiment demonstrates the α-alkoxy esters linking the two epoxide functional groups are quantitatively broken by heating at moderately high temperatures.

Example 7

Thermal Analysis of Cured BGEG Epoxide-Amine Composition

An adhesive composition was prepared by blending together equivalent amounts of BGEG (equivalent weight 210) and PACM (equivalent weight 52.5). Thermal decomposition of the cured compositions was determined by TGA as described in example 4. The results were compared with the corresponding compositions prepared with epoxy monomers BGPP and BPF. The results are presented in Table 4. The data shows that the composition containing BGEG has a slightly higher thermal stability than the corresponding composition containing BGPP. This difference is attributed to the structural variations on the ester group. The material derived from the vinyl ether is slightly more stable than the product derived from the propenyl ether. However both BGEG and BGPP containing compositions degrade at a significantly lower temperatures compared to the composition derived from the conventional epoxide monomer, BPF.

TABLE 4

Comparative TGA Analysis of Cured Epoxide-amine Formulations

| Formulation | $T_d$ (° C.) | Temperature at 10% weight loss (° C.) |
|---|---|---|
| BGEG-PACM | 228 | 258 |
| BGPP-PACM | 216 | 229 |
| BPF-PACM | 372 | 381 |

Example 8

Structural Details of the Cured Epoxy Resins of the Present Invention

This example shows that cured epoxy compositions according to the present invention, cured with an amino-containing curing agent, maintain α-alkoxy ester linkages.

These linkages are thermally labile and provide the reworkable aspect of the invention. In the structures shown below, $R_8$ represents an unreacted bis-α-alkoxy ester which provides the linkage between the two epoxide groups in the epoxy monomers shown in Examples 2, 3 and 5 above; this is a thermally labile site in the cured network polymer and is not present in the final cured polymer structure of cured materials disclosed in U.S. Pat. No. 5,549,932 (Ishidoya). $R_7$ represents the linking group between the amine functional groups of the curing agent and its structure is dependent on the specific epoxy curing agent or agents employed.

SCHEME 1

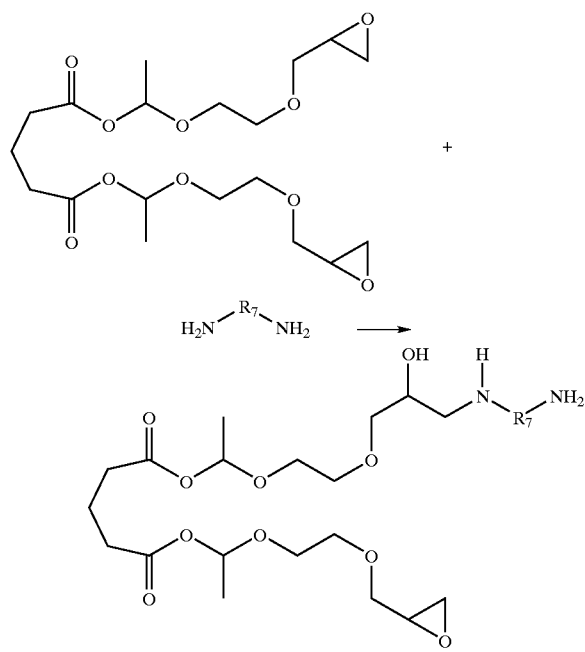

Scheme 1 depicts the initial reaction product of one primary amine with one epoxy function of monomer BGEG (Example 5). This shows the formation of a β-hydroxy amine where the epoxide has undergone a ring opening reaction and the reacted primary amine is converted to a secondary amine. This initial reaction product contains unreacted epoxide and primary amine groups and will react further to give an intermediate linear polymer as depicted generically in Scheme 2, structure A. This polymer has a repeat unit containing alternating $R_7$ and $R_8$ groups interspersed with β-hydroxy amine fragments and is a precursor of the final network structure. It contains active secondary amine sites that can react further with epoxide to give a crosslinked network. This is shown in Scheme 2, structure B where the corrugated lines indicate the points of attachment of the fragment B to the remainder of the network.

SCHEME 2

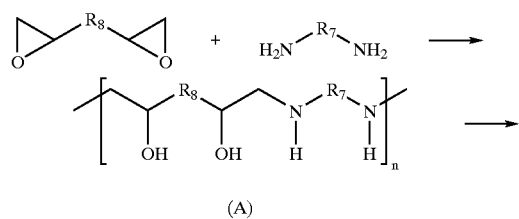

(A)

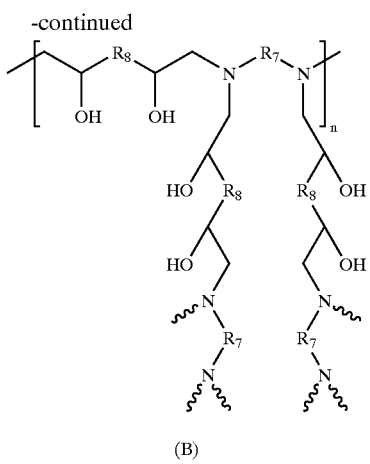

(B)

Primary and secondary amine curing agents are coreactive with the epoxide group. They act as comomomers with the epoxide and are incorporated into the network polymer by a step-growth mechanism. For optimum properties, equivalent amounts of amine and epoxide are generally required, i.e. two moles of epoxide per mole of primary amine and one mole epoxide per mole of secondary amine (see Example 4). Primary amines are generally desired over secondary amines, although blends may also be employed.

In contrast, tertiary amines, imidazoles and related curing agents are generally employed as catalysts or initiators of epoxide polymerization. The mechanism is essentially that of an addition homopolymerization reaction and the structure of the cured product is that of a crosslinked polyether as shown in Scheme 2C. Generally only small amounts of such materials are used (typically 0.01–10% by weight of epoxy) and the amine may be incorporated into the polymer network at the chain ends.

SCHEME 2C

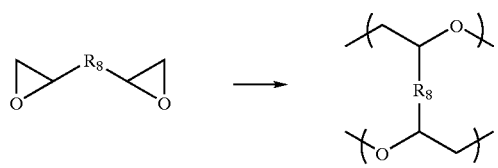

What is claimed is:

1. A curable epoxy composition comprising the reaction product of an epoxidized 1-alkenyl ether or 1-cycloalkenyl ether and a polycarboxylic acid, said reaction product forming a reworkable networked polymer in the presence of a curing agent.

2. The composition of claim 1, wherein the reaction product is substantially free of unreacted acid or acid impurities.

3. The composition of claim 2, wherein said reaction product may be represented by one of the following formulas:

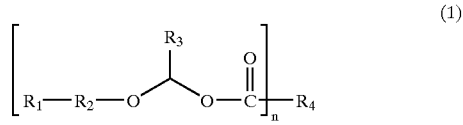

(1)

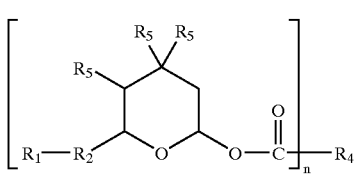

(2)

wherein R₁ is an aliphatic or cycloaliphatic epoxy moiety; R₂ may be a $C_{1-15}$ alkyl, alkenyl, aryl, alkaryl, cycloalkyl, cycloalkenyl, alkyl ether or alkyl ester group; R₃ is a $C_{1-8}$ alkyl, alkenyl, aryl, alkaryl, cycloalkyl, or cycloalkenyl group; R₄ is an n-valent $C_{1-30}$ alkyl, alkenyl, aryl, alkaryl, cycloalkyl, cycloalkenyl, alkyl ether or alkyl thio ether group that is optionally unsubstituted or substituted such as with halogen, hydroxyl or alkoxy groups; R₅ is independently hydrogen, methyl or ethyl groups; and n is an integer from 2 to 4.

4. An epoxy composition comprising:
   (a) a curable epoxy component comprising the reaction product of an epoxidized 1-alkenyl ether or 1-cycloalkenyl ether and a polycarboxylic acid; and
   (b) a curing agent for said epoxy component, wherein reaction products of said epoxy composition are reworkable.

5. The composition of claim 4, wherein said reaction product is substantially free of unreacted acid or acid impurities.

6. The composition of claim 4, wherein said curing agent is an amino-containing agent or a thiol-containing agent.

7. The composition of claim 4, further comprising an inorganic filler component.

8. The composition of claim 4, further comprising a substantially non-reworkable epoxy monomer.

9. The composition of claim 4, wherein said substantially non-reworkable epoxy monomer is selected from the group consisting of a diglycidyl ether of a bisphenol, a polyglycidyl ether of a polyol and a glycidyl ether of a phenol formaldehyde resin.

10. The composition of claim 4, further comprising a material selected from the groups consisting of a flowable agent, an adhesion promoter, a cyanate ester and combinations thereof.

11. The composition of claim 4, wherein said curing agent is selected from the group consisting of amines, imidazoles and combinations thereof.

12. The composition of claim 11, wherein said imidazole is selected from the group consisting of imidazole, isoimidazole, 2-methyl imidazole, 2-ethyl-4-methylimidazole, 2,4-dimethylimidazole, butylimidazole, 2-heptadecenyl-4-methylimidazole, 2-undecenylimidazole, 1-vinyl-2-methylimidazole, 2-n-heptadecylimidazole, 2-undecylimidazole, 2-heptadecylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole, addition products of an imidazole and trimellitic acid, addition products of an imidazole and 2-n-heptadecyl-4-methylimidazole, phenylimidazole, benzylimidazole, 2-methyl-4,5-dephenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4,5-diphenylimidazole, 2-(2-hydroxyphenyl)-4,5-diphenylimidazole, di(4,5-diphenyl-2-imidazole)-benzene-1,4,2-naphthyl-4,5-diphenylimidazole, 1-benzyl-2methylimidazole, 2-p-methoxystyrylimidazole, and combinations thereof.

13. The composition of claim 11, wherein said amine is selected from the group consisting of dicyandiamide, diethylenetriamine, triethylenetetramine, diethylaminopropylamine, m-xylenediamine, diaminodiphenylamine, isophoronediamine, menthenediamine, polyamides, and combinations thereof.

14. The composition of claim 4, wherein said curing agent is a catalytic epoxy resin curing agent used in an amount of from about 0.01 to about 10 percent by weight of said epoxy resin component.

15. The composition of claim 14, wherein said curing agent is an imidazole or a tertiary amine.

16. The composition of claim 4, wherein said curing agent is a primary or secondary amine used in an amount of from about 0.5 to about 2.0 equivalents of amine per equivalent of epoxide.

17. The composition of claim 16, wherein said curing agent is used in an amount of about 1 equivalent of amine per equivalent of epoxide.

18. The composition of claim 4, wherein said curing agent is bis-(para-aminocyclohexyl)methane.

19. The composition of claim 7, wherein said inorganic filler component is selected from the group consisting of materials constructed of or containing reinforcing silicas, aluminum oxide, silicon nitride, aluminum nitride, silica-coated aluminum nitride, boron nitride, and combinations thereof.

20. An epoxy composition comprising:
   (a) a curable epoxy component comprising the reaction product of an epoxidized 1-alkenyl ether or 1-cycloalkenyl ether and a polycarboxylic acid, wherein said reaction product is substantially free of unreacted acid or acidic impurities, and said epoxy component is present in an amount within the range of about 20 to about 65 weight percent, based on the total weight of the composition;
   (b) an inorganic filler component in an amount of about 0 weight percent to about 60 weight percent, based on the total weight of the composition;
   (c) a flowability agent in an amount of about 0 weight percent to about 0.5 weight percent, based on the total weight of the composition; and
   (d) an amino-containing curing agent component comprising a primary or secondary amine compound in an amount of about 0.5 to about 2.0 equivalents of amine per equivalent of epoxide.

21. The composition of claim 20, wherein reaction products of said epoxy composition are reworkable.

22. The composition of claim 20, wherein said epoxy component is a diepoxide selected from the group consisting of bis-(α-glycidoxypropyl) glutarate, bis-(α-glycidoxypropyl) pimelate, bis-[α-(2-glycidoxyethoxy)ethyl]glutarate and combinations thereof.

23. The composition of claim 22 wherein said epoxy component, when cured has an onset temperature of decomposition ($T_d$) of about 216° C. to about 230° C.

24. An epoxy composition which exhibits increased re-workability when cured comprising an epoxy monomer component which is otherwise substantially non-reworkable when cured and an additive which enhances the reworkability of said composition, said additive comprising the reaction product of an epoxidized 1-alkenyl ether or 1-cycloalkenyl ether and a polycarboxylic acid.

25. The composition of claim 24, wherein said additive is a diepoxide selected from the group consisting of bis-(α-glycidoxypropyl) glutarate, bis-(α-glycidoxypropyl) pimelate, bis-[α-(2-glycidoxyethoxy)ethyl]glutarate and combinations thereof.

26. The composition of claim 24 wherein said substantially non-reworkable epoxy monomer component is selected from the group consisting of the diglcidyl ether of bisphenol F, the polyglycidyl ether of a polyol and the glycidyl ether of a phenol formaldehyde resin.

27. A method for synthesizing an epoxy monomer comprising the step of reacting an epoxidized 1-alkenyl ether or 1-cycloalkenyl ether compound with a polycarboxylic acid at a ratio of at least one equivalent of said epoxidized 1-alkenyl ether or said epoxidized 1-cycloalkenyl ether per equivalent of polycarboxylic acid in the absence of acidic catalysts.

28. The method of claim 27, wherein said epoxy monomer is the diepoxide, bis-[α-(2-glycidoxyethoxy)ethyl]glutarate.

29. The method of claim 27, wherein said epoxidized 1-alkenyl ether is 2-vinyloxyethyl glycidyl ether and said polycarboxylic acid is glutaric acid.

30. The method of claim 27, wherein said epoxy monomer is the diepoxide, bis-(α-glycidoxypropyl) glutarate.

31. The method of claim 27, wherein said epoxidized 1-alkenyl ether is 1-propenyl glycidyl ether and said polycarboxylic acid is glutaric acid.

32. The method of claim 27, wherein said epoxy monomer is the diepoxide, bis(α-glycidoxypropyl) pimelate.

33. The method of claim 27, wherein said 1-alkenyl ether is 1-propenyl glycidyl ether and said polycarboxylic acid is pimelic acid.

34. The method of claim 27, wherein said ether compound and said polycarboxylic acid are reacted in the presence of a solvent.

35. A method for preparing a reworkable epoxy composition, which when cured provides a composition which is decomposable, said method comprising admixing:
(a) a curable epoxy component comprising the reaction product of an epoxidized 1-alkenyl ether or 1-cycloalkenyl ether and a polycarboxylic acid; and
(b) an amino-containing or thiol-containing curing agent component.

36. The method of claim 35, further comprising admixing an inorganic filler component.

37. A method of lowering the decomposition temperature of a cured composition of a substantially non-reworkable epoxy resin monomer, said method comprising admixing:
(a) a curable epoxy component comprising the reaction product of an epoxidized 1-alkenyl ether or 1-cycloalkenyl ether and a polycarboxylic acid;
(b) an amino-containing or thiol-containing curing agent component; and
(c) a substantially non-workable epoxy monomer.

38. An electronic device comprising a semiconductor device and a circuit board to which said semiconductor device is electrically connected, said device incorporating in its assembly a reworkable epoxy composition comprising the reaction product of an epoxidized 1-alkenyl ether or 1-cycloalkenyl ether and a polycarboxylic acid.

39. A method of assembling an electronic component comprising applying a reworkable epoxy composition comprising the reaction product of an epoxidized 1-alkenyl ether or 1-cycloalkenyl ether and a polycarboxylic acid to a surface of an electronic component, and permitting said composition to cure.

* * * * *